(12) United States Patent
Fransen

(10) Patent No.: US 6,830,336 B2
(45) Date of Patent: Dec. 14, 2004

(54) AUTOMATED GENERATION OF FUNDUS IMAGES BASED ON PROCESSING OF ACQUIRED IMAGES

(75) Inventor: Stephen R. Fransen, Edmond, OK (US)

(73) Assignee: Inoveon Corporation, Oklahoma City, OK (US)

( * ) Notice: Subject to any disclaimer, the term of this patent is extended or adjusted under 35 U.S.C. 154(b) by 152 days.

(21) Appl. No.: 10/285,805

(22) Filed: Nov. 1, 2002

(65) Prior Publication Data

US 2004/0085514 A1 May 6, 2004

(51) Int. Cl.$^7$ ............................... A61B 3/14; A61B 3/00
(52) U.S. Cl. ....................... 351/246; 351/206; 382/181
(58) Field of Search .................................. 351/200, 205, 351/206, 209, 210, 211, 221, 246; 382/117, 181, 190, 195, 324; 396/18

(56) References Cited

U.S. PATENT DOCUMENTS

| | | | |
|---|---|---|---|
| 4,715,703 A | 12/1987 | Cornsweet et al. | 351/205 |
| 5,649,032 A | 7/1997 | Burt et al. | 382/284 |
| 5,943,116 A | 8/1999 | Zeimer | 351/221 |
| 5,991,444 A | 11/1999 | Burt et al. | 382/232 |
| 5,999,662 A | 12/1999 | Burt et al. | 382/284 |
| 6,296,358 B1 | 10/2001 | Cornsweet et al. | 351/206 |
| 2002/0025145 A1 * | 2/2002 | Nanjyo | 396/18 |
| 2002/0102099 A1 * | 8/2002 | Saito | 396/18 |
| 2002/0176050 A1 * | 11/2002 | Shibata | 351/206 |
| 2003/0234908 A1 * | 12/2003 | Kushida | 351/206 |
| 2004/0051847 A1 * | 3/2004 | Vilser | 351/200 |

OTHER PUBLICATIONS

P. Jasiobedzki, C.J. Taylor, and J.N.H. Brunt, "Automated analysis of retinal images", *Image and Vision Computing*, Apr. 1993; vol. 11, No. 3, pp. 139–144.

Mahurkar et al., "Constructing Retinal Fundus Photomontages. A New Computer–based Method", *Investigative Ophthalmology & Visual Science*, Jul. 1996; vol. 37, No. 8, pp. 1675–1683.

Evans et al., "Tumor Localization Using Fundus View Photography for Episcleral Plaque Therapy", *Medical Physics*, May–Jun. 1993, vol. 20, No. 3, pp. 769–775.

* cited by examiner

*Primary Examiner*—Brian L. Casler
*Assistant Examiner*—John R Sanders
(74) *Attorney, Agent, or Firm*—McDonnell Boehnen Hulbert & Berghoff LLP

(57) ABSTRACT

A method of acquiring images of the ocular fundus includes software processing acquired images to determine which areas of the fundus have been imaged and comparison software for determining which regions of the fundus need to be imaged but have not been thus far. Based on the processing and comparison, audible or visible feedback is provided to the patient prompting them to shift their line of sight so as to enable the capturing of the remaining regions of the fundus.

25 Claims, 6 Drawing Sheets

AUTOMATED GENERATION OF FUNDUS IMAGES BASED ON PROCESSING OF ACQUIRED IMAGES

BACKGROUND OF THE INVENTION

A. Field of the Invention

This invention relates to the field of ophthalmology and in particular to methods and cameras used to acquire images of the interior of the eye and associated anatomical structures.

B. Description of Related Art

The term "ocular fundus" refers to the interior part of the eye, opposite the pupil, where structures including the neurosensory retina, retinal blood vessels, optic nerve, retinal pigment epithelium, and other anatomical structures are located. The appearance of the ocular fundus is affected by a wide variety of pathologies, both ocular and systemic, including diabetic retinopathy, age-related macular degeneration, glaucoma, diabetes, hypertension, arteriosclerosis, and many others. Consequently, most routine physical examinations and virtually all ocular examinations include careful examination of the ocular fundus.

One particular eye disease, diabetic retinopathy, is the leading cause of blindness and partial vision loss in this country. The disease affects patients with diabetes, of which there are some 17 million in the United States, with 800,000 new cases diagnosed each year in the United States alone. Diabetic retinopathy is characterized by specific lesions visible during an examination of the ocular fundus including, microaneurysms, dot blot hemorrhages, venous beading, intra-retinal microvascular abnormalities, neovasculraization, vitreous hemorrhage, and others. Fortunately, if detected and treated early, almost all of the vision loss from diabetic retinopathy is preventable. Hence, early and regular ocular evaluation of patients with diabetes are keys to successful outcomes in this patient population.

Routine examination of the ocular fundus is performed using an ophthalmoscope, a small, hand-held device that shines light through the patient's pupil to illuminate the ocular fundus. The light reflected from the patient's fundus enters the examiner's eye, properly focused, so that the examiner can see the fundus structures. Retinal drawings are typically created by hand showing the location of specific lesions. It is now becoming a more common practice to acquire a permanent record of the appearance of the ocular fundus in the form of a set of digital photographs of various regions of the ocular fundus. The photographs provide a more permanent record of the patient's condition and can be shared among general practitioners and ophthalmologists. They can also be transmitted over networks, enabling remote reading of the images of the ocular fundus by trained readers.

One motivation for acquiring digital photographs of the ocular fundus is the so-called Early Treatment Diabetic Retinopathy Study ETDRS method for diabetic retinopathy staging promulgated by the National Institutes of Health. The ETDRS method calls for photographically acquiring seven, thirty degree, color stereo pair images of the ocular fundus, centralized reading of the photographs, and standardized scoring. The ETDRS standard is an accurate, objective, quantifiable, and reproducible approach to staging this disease, and is considered the "gold standard by which all other methods are judged.

FIG. 1 is an illustration of the seven fields of the ocular fundus that are photographed in an ETDRS diabetic retinopathy evaluation. The seven fields 1–7 are each 30 degrees in size. Field 1 is centered about the optic nerve ON. Retinal blood vessels V are present in each of the seven fields. The vessels V are found in the locations shown relative to the optic nerve in the human population. The spatial location of the vessels V and their position relative to the optic nerve ON, and the appearance and location of the optic nerve ON in the fundus, is grossly the same in the human population.

Cameras for taking pictures of the fundus are known in the art. See e.g., U.S. Pat. No. 6,296,358 and U.S. Pat. No. 4,715,703, the contents of which are incorporated by reference herein. Typically, in such cameras the operator positions the fundus camera at the correct distance from the eye, and such that it is oriented precisely in the vertical and horizontal directions in such a way that the camera's illuminating light rays properly enter the pupil of the patient's eye. A visual target is provided for the patient to look at so that the desired region of the fundus will be imaged. The camera sequentially activates various spatially arranged light sources or targets that the patient looks at to thereby shift their line of sight relative to the optical axis of the instrument. In this manner, the region of interest in the interior of the eye is placed in the optical axis of the instrument and can be captured by the imager in the instrument.

SUMMARY OF THE INVENTION

In a first aspect, a method is provided for imaging the interior of the eye of a patient. The method includes the steps of collecting a series of images of the interior of the eye with a camera and providing visual or audible feedback to the patient to shift their line of sight in order to image additional regions of the interior of the eye. The feedback provided to the patient is derived from processing the series of images already acquired to determine regions of the interior of the eye that have been imaged in the series of images. In response to the patient's reaction to the feedback, the method continues by acquiring additional images of the interior of the eye to thereby acquire additional images of the interior of the eye not previously obtained in the series of images. Thus, the method uses the processing of the images already acquired by the camera in near real time as the mechanism for providing the basis for visual or audible patient feedback to direct the acquisition of additional images of the eye.

The processing of the images will typically require some predetermined instructions or knowledge of what regions of the eye need to be imaged (e.g., the 7 fields of an ETDRS 7 field diabetic retinopathy evaluation, or, as another example, the area extending 40 degrees in all directions from the center of the optic nerve). The instructions for what regions of the eye to image are input into the camera's central processing unit in any suitable form, such as the 7 fields mentioned previously, a circle of particular size in degrees centered about the optic nerve, or any other suitable form. The processing of the images also may require some a priori knowledge of a structure in the eye that can serve as a base for determining which locations in the eye the camera is imaging. Since the optic nerve has in some gross sense the same shape and size characteristics in virtually all humans, the optic nerve is a suitable candidate. If the optic nerve is used, for example, a pattern representing the optic nerve is stored in the computer. Pattern recognition software is used to compare an image or portion thereof acquired by the camera to the stored pattern representing the optic nerve and to therefore confirm that a given exposure of the camera captures the optic nerve or some component part thereof (in which case additional images would need to be generated to image the entire optic nerve).

Once the orientation of the camera relative to a known structure in the eye, e.g., the optic nerve, is determined, the camera can proceed to acquire a set of images covering the regions to be acquired in the imaging session. Each image acquired by the camera will typically overlap with the previous image by some amount (e.g., 5 degrees) so as to maintain some spatial knowledge of what region of the fundus is in the camera's current field of view. The computer or central processing system for the camera executes software that continually compares the acquired imagery to the regions of the eye to be imaged in the imaging session. If gaps in coverage are present, the patient can be provided with additional feedback to shift their line of sight in a manner such that regions that have not been imaged (such as any gaps) are subsequently imaged by the camera.

The method and camera of this invention allows for cameras with a relatively narrow field of view to be used. Such cameras typically have higher quality lenses and other optical components, resulting in improved quality of the acquired images. Improved image quality can result in increased spatial resolution and the ability to detect and analyze finer structures in the eye. Cameras having narrower fields of view also are less expensive. Additionally, the method allows for the images to be captured at a high frame rate reducing the total time to acquire a set of images of the ocular fundus.

In one possible embodiment, the feedback provided to the patient comprises audible instructions to the patient directing the patient to shift their line of sight in a direction derived from the processing of the images. Alternatively, the feedback can comprise an illumination source visible to the patient directing the patient to shift their line of sight in a direction derived from the processing of the images. The illumination source in one possible embodiment is a moveable source.

Some operator input may be used in the method. Thus, in another aspect, a method of imaging the interior of the eye of a patient is provided, comprising the steps of: collecting at least one image in a series of images of the interior of the eye with a camera; processing the images to determine regions of the interior of the eye that have been imaged by the camera; and displaying the at least one image to an operator, e.g., on a screen display associated with the camera. The operator provides input as to additional regions of the interior of the eye that are to be imaged by the camera. The camera is operated and/or the patient is instructed to shift their line of sight in a direction so as to image additional regions of the interior of the eye not previously imaged in the series of images.

In another related aspect, a camera is provided for imaging the interior of the eye. The camera includes a digital imaging device (e.g., CCD video camera) adapted for capturing a series of images of the interior of the eye, and a processing system including software for processing the series of images captured by the digital imaging device to determine regions of the interior of the eye that have been captured by the digital imaging device. The camera further includes comparison software comparing regions determined by the processing software to have been imaged by the camera with a predetermined identification of regions of the interior of the eye of the patient that are to be imaged by the camera. The camera further includes feedback means, such as a speaker providing audible prompts or one or more lights that can be selectively activated, or a moving light source. The feedback means is responsive to the comparison software for operating the camera and/or instructing said patient to shift their line of sight so as to image additional regions of the interior of the eye not previously imaged in the series of images.

The invention is particularly well suited for evaluation of patients for eye diseases including diabetic retinopathy, age-related macular degeneration and glaucoma.

BRIEF DESCRIPTION OF THE DRAWINGS

Presently preferred embodiments of the invention are described below in conjunction with the appended drawing figures, where like reference numerals refer to like elements in the various views, and wherein.

DETAILED DESCRIPTION OF PREFERRED EMBODIMENTS

In a first and primary aspect, a method of imaging the interior of the eye of a patient is provided. A series of images of the interior of the eye is acquired with a camera. Feedback is provided to the patient directing them to shift their line of sight. The feedback is derived from processing the series of images to determine regions of the interior of the eye that have been imaged in the series of images. In response to the patient's reaction to the feedback (i.e., their shifting their line of sight), the method continues with acquiring additional images of the interior of the eye to thereby acquire additional images of the interior of the eye that were not previously obtained in the series of images.

The present invention will be described in the context of a presently preferred fundus camera, which is basically similar in design to the Cornsweet et al. U.S. Pat. No. 6,296,358. Some aspects of that disclosure that are not pertinent to the present discussion have been omitted for purposes of brevity and clarity. It will be appreciated that the invention can be practiced by appropriate modification to the software and/or hardware of other fundus cameras generally, including those made by companies such as Topcon, Zeiss, Cannon, and Nidek. The mechanical and optical details are not particularly important, and the only requirement is that the camera include software and a processing unit for processing the acquired images as discussed in detail below. The following detailed description is provided by way of illustrating a currently preferred fundus camera and camera computer system, but it is not meant to limit the scope of the invention. The scope of the invention is set forth in the claims, which encompass cameras which depart from the specifics of many of the optical and mechanical features set forth below.

Figure 2:
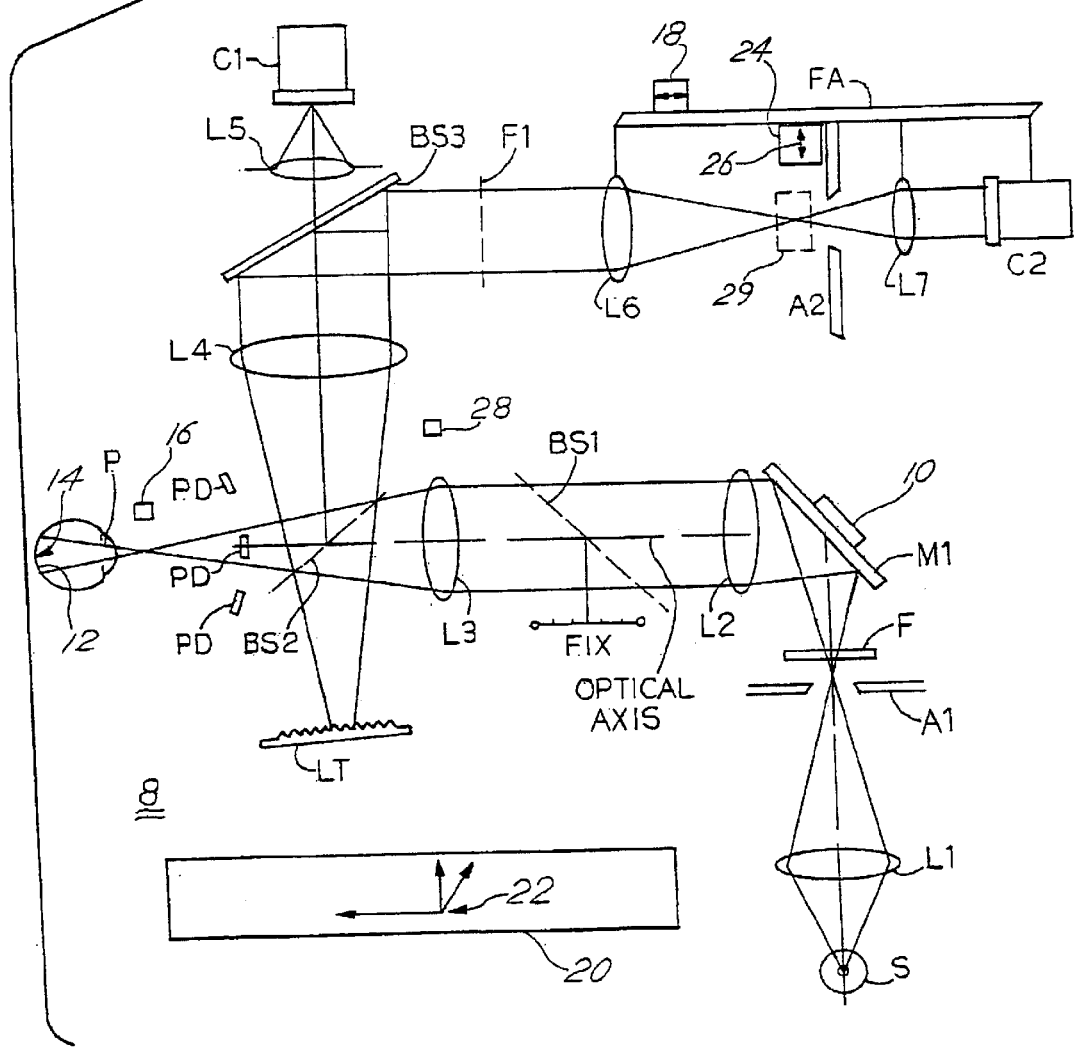
FIG. 2 is a schematic diagram of a fundus camera that can be used to obtain images of the fundus shown in FIG. 1.

Referring to FIG. 2, there is illustrated a representative example of a camera used for capturing images that can be used with the system and method of the present invention. Lens L1 focuses light from a light source S onto a small aperture A1. The light source may be a source of visible light, infrared radiation or of a wavelength in the near visible infrared region. Light passing through aperture A1 passes through a filter F and is reflected by mirror M1 toward lens L2. Mirror M1 is pivotally mounted to permit rotation about two orthogonal axes, which pivotal mounting is represented by device 10 attached to the mirror. Lens L2 collimates (makes parallel) light from aperture A1. A beam splitter BS1 transmits about ninety percent (90%) of the incident light from lens L2 to lens L3. Half of the light passing through lens L3 is reflected by beam splitter BS2 and is absorbed by light trap LT. The other half of the light passing through lens L3 forms an image of aperture A1 in the focal plane of lens L3, which focal plane lies in the plane of a patient's pupil P. The light passing through the pupil illuminates a section 12 of ocular fundus 14 (hereinafter only the term fundus will be used).

Light diffusely reflected from fundus 14 emerges from pupil P and half of it is reflected by beam splitter BS2 toward collimating lens L4, which lens is at its focal distance from the pupil. About ten percent (10%) of the light is transmitted through beam splitter BS3, which light passes through lens L5. Lens L5 forms an image of the pupil and the front of the eye in the plane of a video sensor C1. The video output from video sensor C1 is displayed on an operator's monitor (on computer screen shown in FIG. 3) to provide a view of the eye and of the pupil and provide input image data for automatically focusing and tracking the patient's pupil.

If the patient's eye is focused at infinity, the light reflected from each point on fundus 14 will be collimated as it is incident on lens L4. Therefore, 90% of the light reflected from beam splitter BS3 will form an aerial image of the fundus in the focal plane of lens L4, which focal plane is represented by a dashed line identified as FI (Fundus Image). The light passes through lens L6, which lens is at its focal distance from fundus image FI. Thus, lens L6 will collimate light from each point on the fundus. Further, because the light considered as originating in the plane of pupil P is collimated by lens L4, lens L6 will form an image of the pupil in its back focal plane, which is coincident with the location of second aperture A2. Light passing through second aperture A2 is incident on lens L7, which lens will then form an image of the fundus in its back focal plane, which is coincident with second video sensor C2. The video image produced by video sensor C2 represents an image of the fundus.

If the eye is not focused at infinity, the aerial fundus image FI will be moved away from the back focal plane of lens L4. For example, if the eye is nearsighted, the aerial fundus image will move toward lens L4. Such movement would cause the fundus image to be defocused on video sensor C2. Focusing the image under these conditions is accomplished as follows. Lens L6, aperture A2, lens L7, and video sensor C2 are mechanically connected to one another by a focusing assembly labeled FA; that is, these elements are fixedly positioned relative to one another and move as a unit upon movement of the focusing assembly. A unit identified by reference numeral 18 provides rectilinear movement of the focusing assembly on demand.

The entire optical system (8) discussed above and illustrated in FIG. 2 is supported upon an assembly identified by reference numeral 20. The assembly includes motive elements, such as rectilinear actuators and related servo-mechanisms responsive to commands for translating the entire optical system horizontally (laterally), vertically and toward and away from the eye, as representatively depicted by set of arrows 22.

Aperture A2 is moveable horizontally as indicated by arrows 26 by means of an actuator 24, enabling the capture of stereo pairs of images at each location of the fundus.

Figure 3:
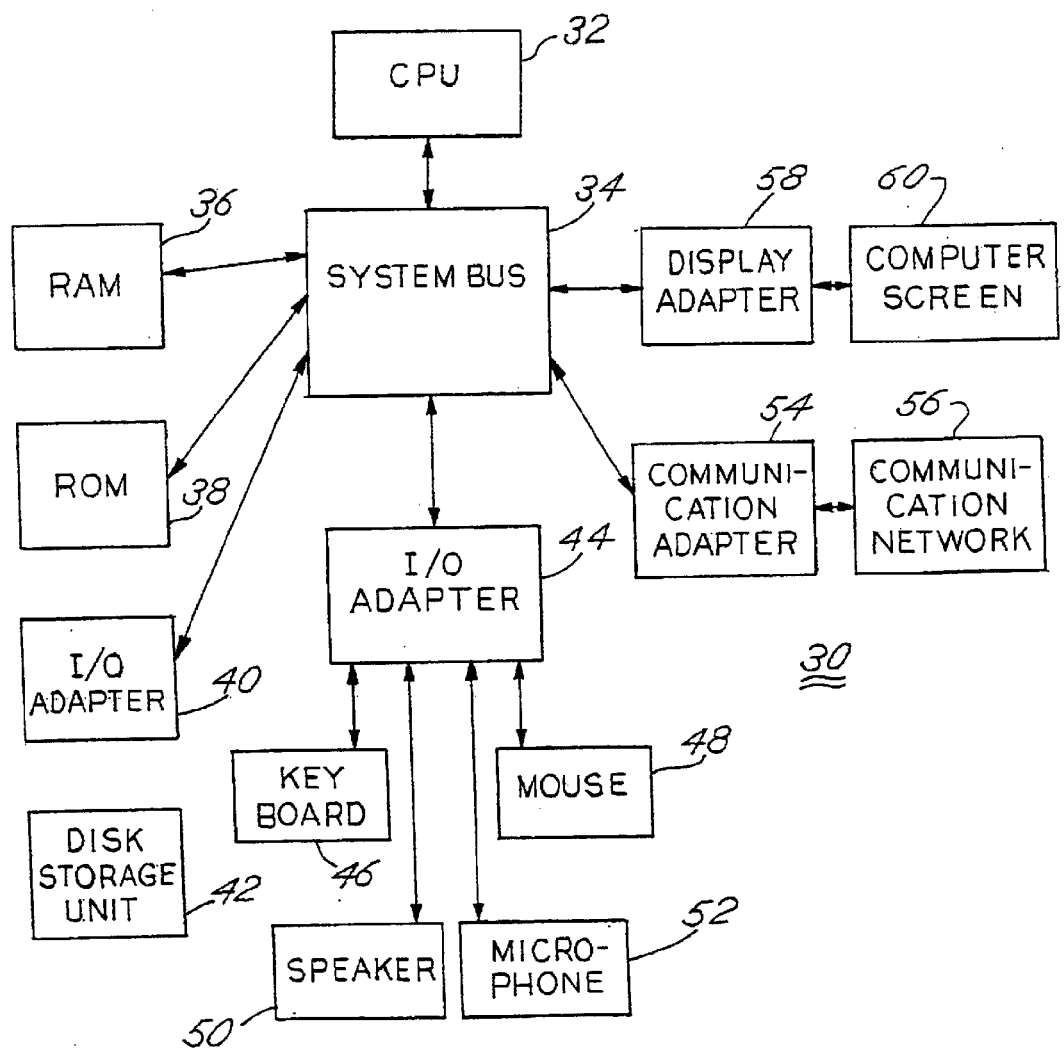
FIG. 3 is a block diagram of the electronics that are used in the camera of FIG. 2.

To operate optical system 8, a computer control system 30 is required, which is representatively illustrated in FIG. 3. The computer control system includes a central processing unit (CPU) 32, such as a microprocessor, and a number of units interconnected via a system bus 34. A random access memory (RAM) 36, a read only memory (ROM) 38 are incorporated. An input/output adapter 40 interconnects peripheral devices, such as a disk storage unit 42. A user interface adapter 44 connects the keyboard 46, a mouse (or trackball) 48, a speaker 50, a microphone 52, and/or other user interface devices, such as a touch screen (not shown) with system bus 34. A communication adapter 54 interconnects the above-described optical system 8 through a communication network 56. A display adapter 58 interconnects a display unit 60, which maybe a video screen, monitor, or the like. The computer operating system employed may be any one of presently commercially available operating systems.

In operation, an operator enters patient information data into the computer control system using the keyboard. The operator also enters the location or set of locations on the fundus that are to be imaged in the evaluation. It may be noted that the field of view of the optical system can for example be 30 degrees in diameter or less, for example 15 degrees, while the ocular fundus is about 200 degrees in diameter. To image various regions of the 200-degree fundus, the eye is rotated with respect to the optical system. Such rotation of the eye is achieved by providing feedback to the patient from processed images that prompt the patient to look from one reference point to another, for example in response to voice commands (e.g., "look up and to the right", "look a little further to the right", etc.) or by providing visible fixation targets as described below.

After entry of the raw data, the patient's head is juxtaposed with a head positioning apparatus to locate the eye in approximate alignment with respect to the optical axis. An image of the front of the eye including the patient's pupil produced by video sensor C1 appears on computer screen 60. The operator may use a trackball or mouse 48 or similar control to move the image horizontally and vertically until the pupil is approximately centered on a set of cross-hairs displayed on the computer screen. Such horizontal and vertical movements, along with focusing of the image of the pupil, are achieved by moving the entire optical system 8 through energization of assembly 20 (see FIG. 2). That is, the horizontal and vertical movements of the image are achieved by moving the entire optical system horizontally and vertically and the focusing of the pupil image is accomplished by moving the entire optical system toward or away from the eye. When the operator is satisfied that the pupil image is approximately centered, the operator initiates the automatic pupil focus, alignment and image collection procedure. Further details regarding the construction and operation of the camera illustrated in FIGS. 2 and 3 is found in Cornsweet et al., U.S. Pat. No. 6,296,358, the content of which is incorporated by reference. Further details are not particularly pertinent to the present discussion.

The subject camera provides the ability to provide feedback to the patient to direct their line of sight in a direction so as to select the fundus region to be imaged. One mechanism for providing feedback is through instructions from the operator or through computer generated voice commands delivered via a speaker, such as shown in FIG. 3 at 50. Alternatively, the illustrated embodiment may include a set of visible LEDs arranged in a two-dimensional array indicated as FIX in FIG. 2. Beam splitter BS1 reflects about 10% of the light from these LED's toward lens L3 and the eye. The set of dots (FIX) lies in the back focal plane of lens L3 and these LED's appear to the eye as if they were a long distance away. Only one of the LED's is illuminated at any given time and the patient is asked to look at it. When the patient looks at the illuminated LED, the location of the LED with respect to the optical axis of the instrument determines the location on the fundus that will be illuminated and imaged. For example, if the LED that lies on the optical axis is turned on and the patient fixates it, then the image will be centered on the fovea or macula. If the illuminated LED is 17 degrees to the patient's left, then the region of the fundus imaged has its center 17 degrees to the left of the macula (as observed from the front of the eye).

Figure 1:
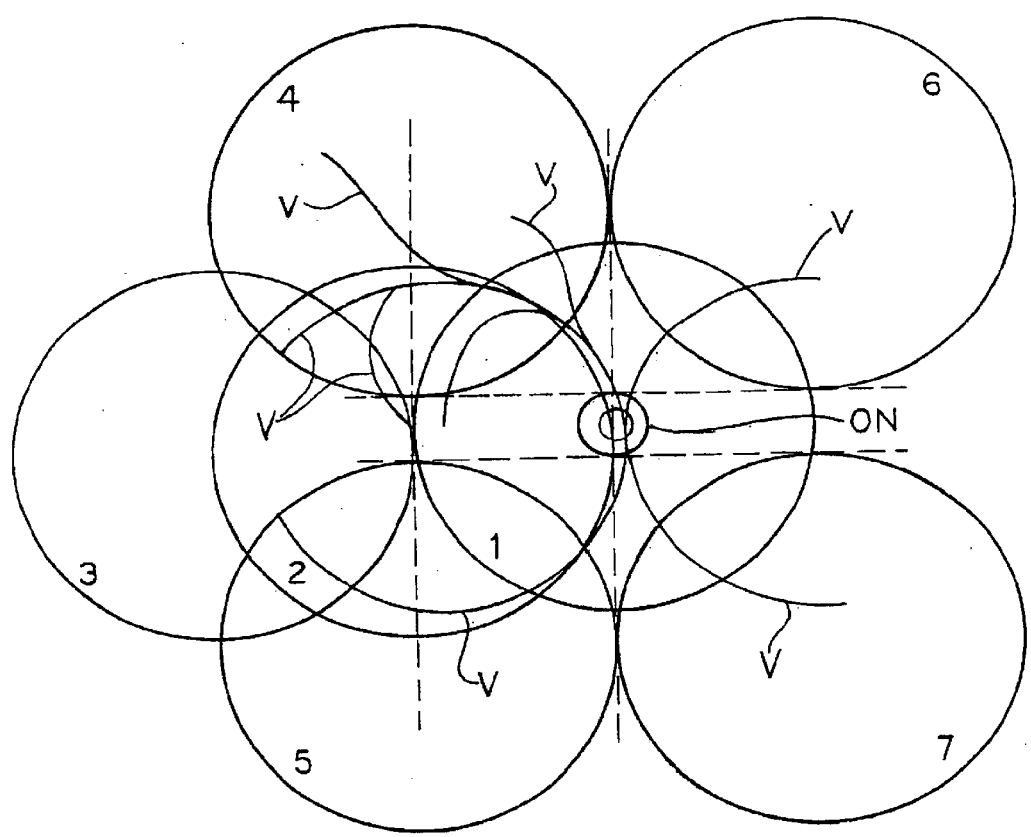
FIG. 1 is an illustration of seven fields of the ocular fundus of the right eye that should be imaged for purposes of diabetic retinopathy evaluation in accordance with the ETDRS standard.

In addition to the LED's in the plane labeled FIX, other visible LED's, such as LED 28 shown in FIG. 1, are positioned at various angular displacements from the optical axis, lying, such as to the sides of lens L3. When one of these LED's is turned on, it does not appear at optical infinity but nevertheless the patient can successfully fixate it to yield a view of more peripheral fundus features.

An alternative moveable fixation target can be used, such as for example the end of a single fiber optic strand or fiber optic bundle or the projection of a liquid crystal or other type of light emitting display whose contents can be changed. Light from either of these devices is projected to reflect from the beam splitter B1 in FIG. 1 towards lens L3 and the eye. The fiber optic tip is provided with a suitable X-Y motor controller and motorized stage or other positioning device to move the fiber optic tip anywhere in the plane indicated by FIX. The movement of the fiber optic tip is controlled based on the processing of the acquired images to be in a particular location such that, when the patient directs their line-of-sight to the fiber optic tip, a desired region on the interior of the eye is imaged. Persons skilled in the art will be able to construct such a moveable source from the teachings herein.

Figure 4:
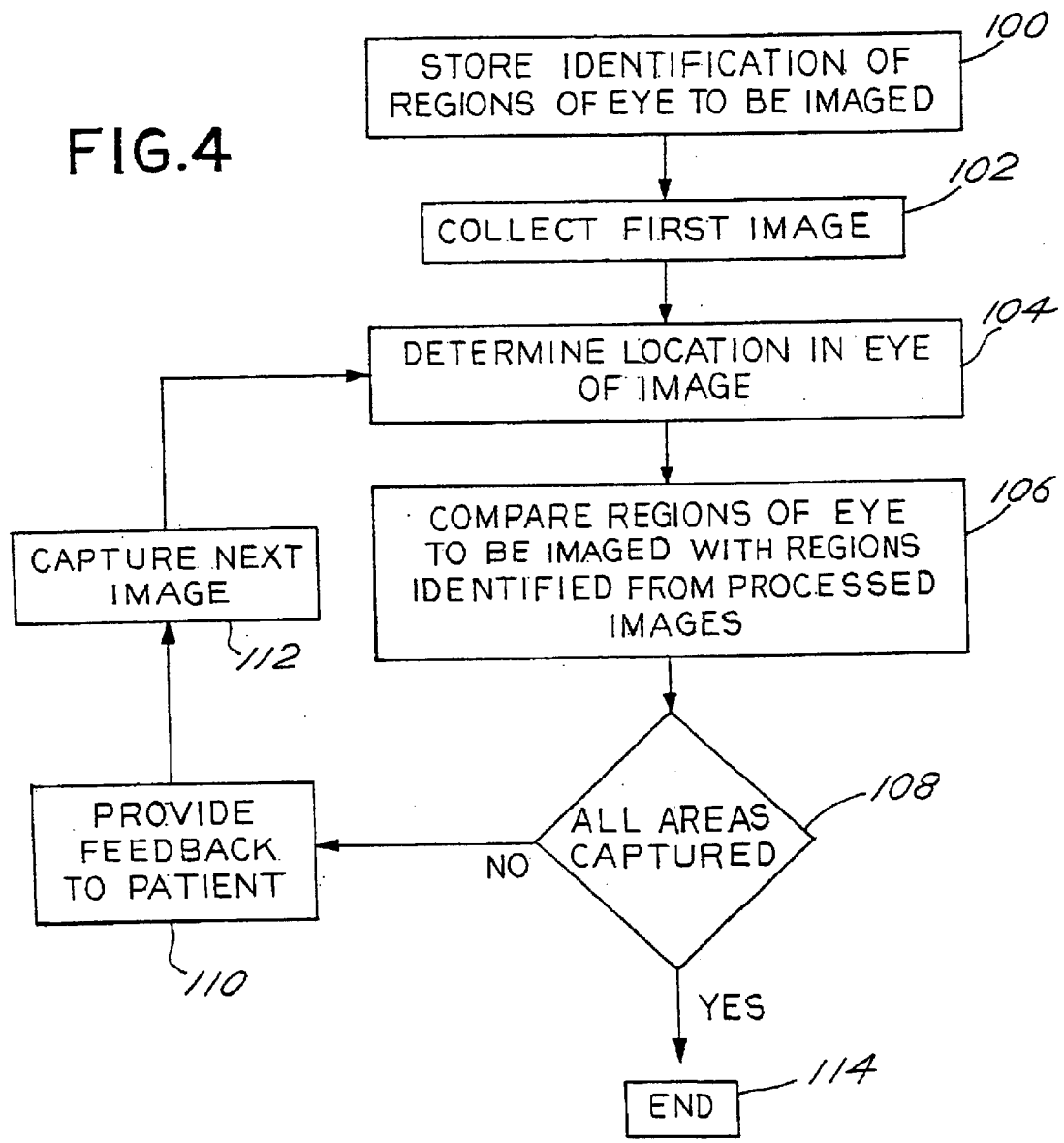
FIG. 4 is a flow chart illustrating a method of obtaining a set of images of the eye in accordance with a presently preferred embodiment of the invention.
Figure 5A:
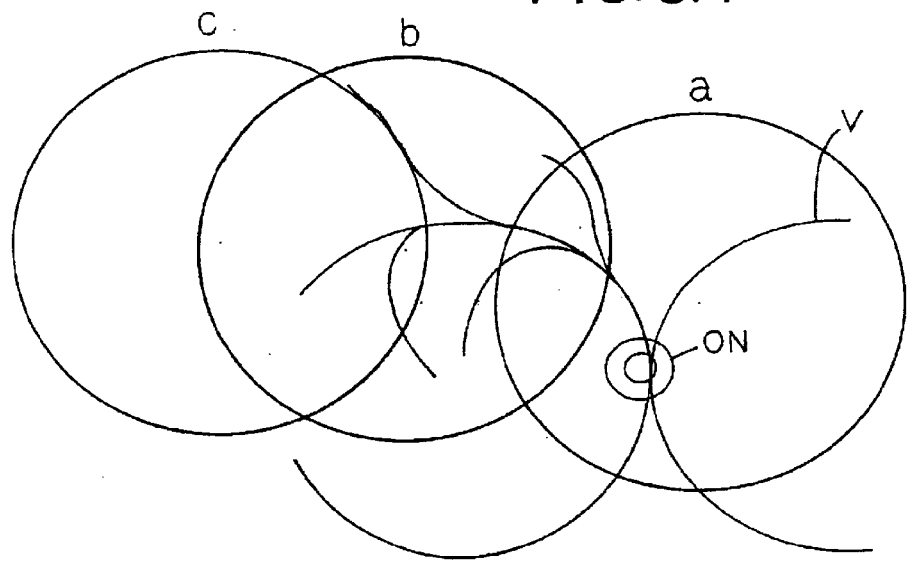
FIGS. 5A and 5B show the first 3 images acquired in the series of images in one possible example of the invention.
Figure 5B:
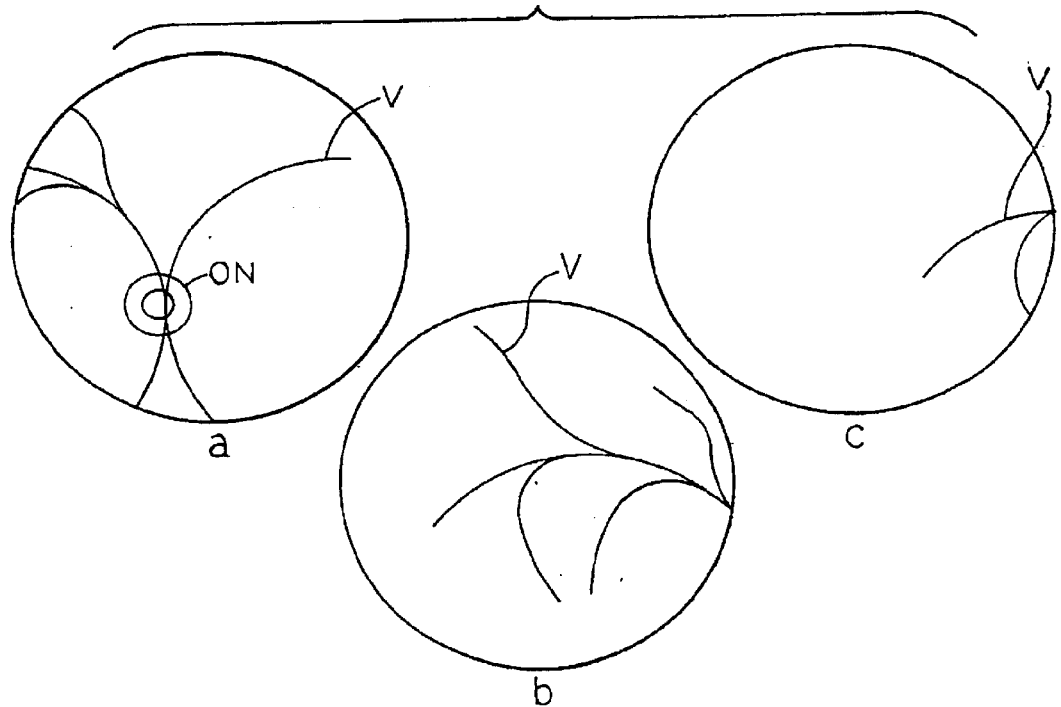

The operation of the instrument to collect images will now be described with reference to FIGS. 4–6. At step 100, when the operator sets up the instrument prior to collecting images of a particular patient, information is stored as to the region or set of regions of the fundus to be imaged. This information could be retrieved from a database, provided from an external source (such as via email from a primary care physician or ophthalmologist) or entered manually by the operator. In any event this information is stored in the computer system of FIG. 3, e.g., in the RAM memory 36. The patient is placed in front of the camera in a position for acquiring a first image by the camera C2 of FIG. 2. The first image is then obtained, step 102. Typically, the first image will be centered about or will at least contain the macula of optic nerve, and will be acquired with the use of one of the fixation lights FIX in FIG. 2. The captured image is stored in the memory of the computer system. At step 104, a determination is made of the location in the eye of the captured image. As noted above, the optic nerve has a distinct visual appearance in virtually every patient. The computer system includes pattern recognition software that compares the captured image with a pattern representing the appearance of the optic nerve in the fundus. By using suitable cross-correlation or pattern matching algorithms in the computer system, the computer system can determine that the first image includes the optic nerve and further determine the orientation of the optic nerve in the image. This first image is image "a" in the example of FIG. 5A and 5B.

Next, at step 106, the computer system conducts a comparison of the region of the eye to be imaged with the regions identified in step 104. In the present example, assume that the operator indicated that all seven fields of an ETDRS diabetic retinopathy evaluation need to be imaged. The comparison indicates that the captured image is only part of one of the seven fields. At step 108, the result of the comparison is a determination of whether all regions of the fundus have been imaged.

If all the regions have not imaged, the patient is provided with feedback at step 110 to change their line of sight so as to enable additional regions of the fundus to be imaged. For example, the instrument may provide audible instructions to the patient to shift their line of sight. Alternatively, a new fixation target may be activated, or a moveable fixation target moved, so as to shift the patient's line of sight in a new direction. At step 112, another image is captured. The second image overlaps the first image at least to some extent to avoid gaps in coverage and allow a seamless reconstruction of the overall image to be performed. Furthermore, cross-correlation procedures can be used between the second and the first image to register the images to each other to as to enable generation of a composite or overall mosaic image. In the example in FIGS. 5A and 5B, a second image "b" is generated. Note that in FIG. 5A image "b" overlaps image "a" by approximately 10 to 15 percent. The amount of overlap can vary.

Returning to FIG. 4, the process loops back to step 104, and a comparison is again performed of the regions of the eye to be imaged and the regions captured by the combined images "a" and "b". At step 108, a determination is made of whether all the regions to be imaged have been captured. Steps 110, 112, 104, 106 and 108 are repeated until the result of step 108 is that the entire region of the fundus to be imaged has been completely imaged. In FIGS. 5A and 5B, a third image "c" is obtained that overlaps with the second image "b", and the process described above with reference to FIGS. 4 and 5A and 5B continues until all the regions in the seven fields have been imaged. It will be apparent from the process illustrated in FIGS. 5A and 5B that each new region imaged will require the patient to shift their line of sight to a new orientation, typically by audible and/or visual feedback.

Figure 6:
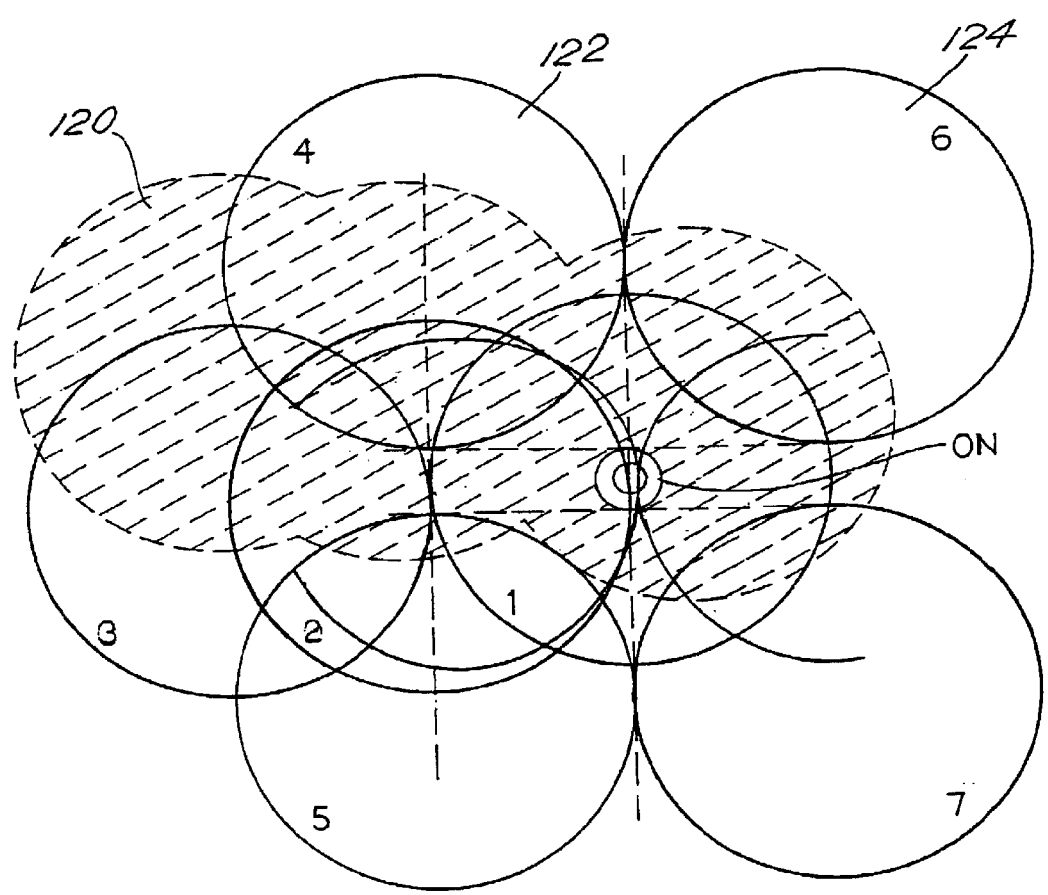
FIG. 6 is an illustration of a series of three images that have been captured by the camera of FIG. 2, and indicating additional areas of the ocular fundus that have not been imaged; the computer provides feedback to the patient and/or operates the camera so as to acquire images of the areas not previously imaged.

FIG. 6 shows the seven fields 1–7 to be imaged in the illustrated example. The region 120 shown in shading represents the regions captured in the first three images shown in FIGS. 5A and 5B. In the comparing step 106, performed after the third image "c" has been acquired, the software will determine that numerous regions remain to be imaged, including region 122 in field 4 and region 124 in field 6. To image region 122, the operator or computer system may instruct the patient to "look up and slightly to the left"; or alternatively a fixation light may be activated that would cause the patient to direct their line of sight in a direction such that region 122 is captured next. For example, a moveable fixation light would move in the plane of fixation FIX to a location such that the desired region is in the field of view of the camera. Alternatively, the software could be written such that another image is captured which includes the optic nerve, but is designed to image in the lower left quadrant and cover portions of regions 1, 2 and 5, and three overlapping images would be obtained similar to images "a", "b", and "c", but rotated say 20 degrees counterclockwise from the regions 120 covered in images "a", "b" and Still other strategies for capturing all the regions to be imaged could be developed. One might be to simply ask the patient to look straight ahead first and then in all directions, and operate the camera C2 to capture the images as the patient looks ahead and around in a quasi random manner. After a certain percentage of the regions have been imaged, say 80 percent, or after a predetermined lapse of time, the software would direct the patient to look in specific directions to capture the remaining gaps in coverage. In this alternative, again there is a processing of the acquired images and feedback is provided to the patient based on the acquired images to fill in gaps in coverage.

As another example, the camera may take the first image, for example a 30-degree image of field 1 centered on the optic nerve. The software could calculate the number of pixels in the array per degree at the optic nerve and fovea, and the number of pixels per degree at the periphery of field. Such calculation would require knowledge of the field of view of the CCD, the number of pixels in row and column directions, and some knowledge or assumptions regarding the geometry of the interior of the eye. Based on these calculations, and a comparison of the regions so far acquired with the regions to be imaged, the computer system could determine the locations where the line of sight needs to be shifted and provide the appropriate feedback to the patient to shift their line of sight in the desired manner (e.g., "look down and to the right", activate a particular fixation light in an array of lights, or provide a moving fixation light that moves to an appropriate position).

In all of the above examples, the invention will typically make use of a priori knowledge of what regions are to be captured where it is desired to image specific regions whose definition is based on a priori knowledge, for example knowledge of what the optic nerve (or some other known object) looks like and where it is in the fundus. Such a priori knowledge is needed in order to make an intelligent comparison of the captured images and the regions to be captured. Fortunately, the characteristics of the optic nerve are unmistakable. The optic nerve thus serves as a convenient reference for the first image, and a starting point for building an overall composite image based on the acquired images. Once the optic nerve is acquired in the first image, the rest of the images should preferably overlap by some amount (e.g., 5–10 degrees) so as to minimize gaps in coverage, enable the cress-correlation or other algorithms to work to form a composite image, and provide for sub-pixel spatial resolution in the resulting images.

However, there may be some instances in which no a priori knowledge of any particular structure in the eye is required. For example, it may not be absolutely necessary to have prior knowledge of the optic nerve's location on the retina or even prior knowledge of its shape or size. Rather, what would be required is adequate structure or features to support the operation of the image mosaicing algorithms. These adequate structures or features may consist merely of a minimum overlap between adjacent field of view images so that the individual images can be pieced together and registered to each other to create a composite mosaic. It may be possible to image all the pertinent portions of the interior of the eye, using overlapping images, and using the processed images to provide feedback to the patient to eliminate gaps in coverage, without storage of any patterns, e.g., representing a "typical" optic nerve or other structures.

With the method and apparatus of this invention, a smaller field of view camera for the imaging camera C2 is possible. In a representative embodiment, the camera field of view is smaller than 30 degrees and may be 15 degrees or even less. With a smaller field of view, it is easier to design an optical system with minimal aberrations or other imperfections. Also, smaller fields of view enable the use of lower cost CCD sensors. The overall instrument can be smaller. Additionally, due to the higher quality optics possible with smaller field of view cameras, the overall image quality is higher. Further, sub-pixel spatial resolution techniques can be used where there is overlap between images. With low cost CCD sensors, including ones that operate at video frame rates, there can be overlap between images throughout the entire fundus. These capabilities can enhance both the spatial resolution of the image (the ability to detect and observe fine details such as microaneurysms), and also can be used to enhance the contrast of images using signal averaging techniques.

The reader is directed to the following references for teachings of methods for generating composite mosaic images, which may be used by the CPU of the computer system for piecing together the series of images captured by the CCD camera. See U.S. Pat. Nos. 5,999,662; 5,991,444; 5,943,116 and 5,649,032, the contents of which are incorporated by reference herein. Other references specifically disclosing image mosaic techniques are set forth in Evans et al., *Tumor localization using fundus view photography for episcleral plaque therapy*, Med Phys 1993 May–June; 20(3): 769–75; Mahurkar et al., *Constructing retinal fundus photomontages. A new computer-based method*; Invest Ophthalmol Vis Sci 1996 July; 37(8): 1675–83. The content of these references is also fully incorporated by reference herein. The development of software for pattern recognition, generation of a mosaic image, and comparison of a composite image to an image or description of the regions to be acquired are considered within the ability of persons skilled in the relevant art in view of the description herein and the knowledge of persons skilled in the art.

The invention can be implemented with varying degrees of automation. In particular, in one possible embodiment, the acquisition of images, and providing of feedback to the patient, could be completely automated and involve essentially no operator involvement. The method steps shown in FIG. 4 would essentially be coded in software and executable by the central processing unit of FIG. 3. The specified regions of the interior of the eye to be imaged would be entered into the camera prior to the start of the imaging session. This could be entered in terms of a specified field of view (degrees) about a known structure (center, top or bottom of the optic nerve, or center of a macula) in which case the central processing unit must have prior knowledge of the structure of the interior of the eye. Since the optic nerve has grossly the same location, shape and size characteristics in virtually all humans, the optic nerve is an attractive candidate as a point of reference. The center of the macula could be an alternative point of reference. In this embodiment, the central processing unit would terminate the acquisition of images after determining that all specified regions of the interior of the eye have been imaged in the series of images.

On the other hand, the invention may provide for considerable operator involvement. For example, as the images are acquired the computer system generates a composite mosaic image of the fundus and presents it to an operator on a computer screen or other display associated with the instrument. The display would preferably show the areas to be imaged in the evaluation of the patient. The region 120 shown shaded in FIG. 6 would be the composite mosaic image already acquired from the patient, and the outline of the fields to be acquired in the screening session would also be shown in the display. The operator would then provide input to the computer system using the keyboard, mouse, voice prompts, or otherwise indicating the additional areas that need to be imaged, such as by typing or entering coordinates, typing in fields to be acquired, entering degree information, highlighting areas with a mouse, or any other type of action that indicates the additional regions that need to be captured. The camera is then operated to acquire the additional areas such as by providing the appropriate visible or audible prompts to cause the patient to shift their line of sight to image the regions that still needed to be obtained. In this embodiment, the camera would continue imaging additional regions of the interior of the eye, as prompted by the operator, until the operator terminates the acquisition of the images.

Variations from the disclosed preferred and alternative embodiments are contemplated as being within the scope of the invention. The optical and mechanical design of the fundus camera is generally not critical. Additionally, the camera can be used to capture stereo pairs of images at each location of the fundus. Furthermore, video cameras capturing true color images could be used. The true scope of the invention will be apprehended by reference to the appended claims.

I claim:

1. A method of imaging the interior of the eye of a patient, comprising:
   a) collecting a series of images of the interior of the eye with a camera;
   b) providing feedback to the patient, the feedback derived from processing said series of images to determine regions of the interior of the eye that have been imaged in said series of images;
   c) responsive to the patient's reaction to the feedback, acquiring additional images of the interior of the eye to thereby acquire additional images of regions of the interior of the eye not previously obtained in said series of images.

2. The method of claim 1, wherein said feedback comprises audible instructions to the patient directing the patient to shift their line of sight in a direction derived from processing said images.

3. The method of claim 1, wherein said feedback comprises an illumination source visible to the patient directing the patient to shift their line of sight in a direction derived from the processing of said images.

4. The method of claim 1, wherein said method is performed in an evaluation of the patient for diseases affecting the eye.

5. The method of claim 4, wherein said diseases affecting the eye are selected from the group of diseases consisting of diabetic retinopathy, age-related macular degeneration and glaucoma.

6. The method of claim 1, wherein said camera comprises a digital camera having a field of view of less than 30 degrees.

7. The method of claim 6, wherein said camera has a field of view of less than or equal to 15 degrees.

8. A method of imaging the interior of the eye of a patient, comprising:
   a. collecting a series of images of the interior of the eye with a camera;
   b. processing said series of images to determine regions of the interior of the eye that have been imaged by said camera in said series of images;
   c. comparing said regions determined in step b. with a predetermined identification of regions of the interior of the eye of the patient that are to be imaged by said camera;
   d. in response to said comparing step, operating said camera and/or instructing said patient to shift their line of sight in a direction so as to image additional regions of the interior of the eye not previously imaged in said series of images.

9. The method of claim 8 wherein said method is performed in an evaluation of the patient for diseases affecting the eye.

10. The method of claim 9, wherein said diseases affecting the eye are selected from the group of diseases consisting of diabetic retinopathy, age-related macular degeneration and glaucoma.

11. The method of claim 8, wherein said camera comprises a digital camera having a field of view of less than 30 degrees.

12. The method of claim 11, wherein said camera has a field of view of less than or equal to 15 degrees.

13. A method of imaging the interior of the eye of a patient, comprising:
   a. collecting at least one image in a series of images of the interior of the eye with a camera;
   b. processing said at least one images to determine regions of the interior of the eye that have been imaged by said camera;
   c. displaying the said at least one image to an operator;
   d. receiving input from said operator as to additional regions of the interior of the eye that are to be imaged by said camera; and
   e. operating said camera and/or instructing said patient to shift their line of sight in a direction so as to image additional regions of the interior of the eye not previously imaged in said series of images.

14. A camera for imaging the interior of the eye, comprising:
   a digital imaging device adapted for capturing a series of images of the interior of the eye;
   an optical system for directing light from the interior of the eye onto said digital imaging device;
   a processing system including software for processing said series of images captured by said digital imaging device to determine regions of the interior of the eye that have been imaged by said digital imaging device;
   comparison software comparing said regions determined by said processing step with a predetermined identification of regions of the interior of the eye of the patient that are to be imaged by the camera;
   feedback means responsive to said comparison software operating said camera and/or instructing said patient to shift their line of sight so as to image additional regions of the interior of the eye not previously imaged in said series of images.

15. The camera of claim 14, wherein said feedback means comprises an illumination source visible to the patient directing the line of sight of the patient in a direction derived from the processing of said images.

16. The camera of claim 14, wherein said feedback means comprises a source of audible instructions to the patient directing the patient to shift their line of sight in a direction derived from the processing of said images.

17. The camera of claim 14, wherein said digital imaging device has a field of view less than 30 degrees.

18. The camera of claim 16, wherein said digital imaging device has a field of view of less than 15 degrees.

19. The camera of claim 14, wherein said series of images comprise a series of overlapping images, and wherein said processing system comprises software for enhancing the spatial resolution and/or contrast of said images by processing overlapping portions of said images.

20. The camera of claim 14, wherein said series of images comprises a first image and a second image, wherein said first image comprises an image of the optic nerve of the patient, and wherein said second image overlaps said first image.

21. The camera of claim 14, wherein at least one of said images comprises an image of the optic nerve of the patient, and wherein said software includes pattern recognition software for recognizing the image of the optic nerve.

22. The camera of claim 14, wherein said feedback means comprises a moveable illumination source visible to the patient directing the line of sight of the patient in a direction derived from the processing of the images.

23. The camera of claim 22, wherein said moveable illumination source comprises a fiber-optic light source.

24. The camera of claim 22, wherein said moveable illumination source comprises a light emitting display whose contents can be changed to thereby provide a moveable fixation target.

25. The camera of claim 24, wherein said light emitting display comprises a liquid crystal display (LCD) device.

* * * * *